United States Patent [19]
Miraldi et al.

[11] Patent Number: 5,429,800
[45] Date of Patent: Jul. 4, 1995

[54] MICRO-ISOLATOR STEAM STERILIZATION CYCLE AND APPARATUS

[75] Inventors: Peter T. Miraldi, Erie; William R. Barron, McKean; Anthony B. Ruffo, Erie, all of Pa.

[73] Assignee: American Sterilizer Company, Erie, Pa.

[21] Appl. No.: 160,500

[22] Filed: Dec. 1, 1993

[51] Int. Cl.⁶ .................... A61L 2/06; G05D 16/00
[52] U.S. Cl. ........................... 422/26; 422/33; 422/110; 422/112; 119/18
[58] Field of Search ............... 119/15, 17, 18; 435/287; 422/26, 33, 292, 298, 299, 108, 109, 110, 112, 113; 53/431

[56] References Cited

U.S. PATENT DOCUMENTS

| | | |
|---|---|---|
| 4,108,601 | 8/1978 | Wolff . |
| 4,166,096 | 8/1979 | Gillis . |
| 4,238,447 | 12/1980 | Wolff . |
| 4,971,764 | 11/1990 | Albright ................ 422/26 |

OTHER PUBLICATIONS

"Validation of Steam Sterilization Cycles", *PDA Technical Monograph No. 1*, Parenteral Drug Association Research Committee and Task Groups, 1978.

*Primary Examiner*—Robert J. Warden
*Assistant Examiner*—E. Leigh Dawson
*Attorney, Agent, or Firm*—Jones, Day, Reavis & Pogue

[57] ABSTRACT

A particularly useful method is disclosed for sterilizing micro-isolators in which a sipper bottle is contained. In the present invention, sterilization is effected by using a microprocessor control to regulate the pressure within a sterilization chamber in response to temperature conditions. Pressure within the chamber is regulated so that as temperature is raised and lowered, the boiling point of water in the sipper bottle is never exceeded. Prior to sterilization, the chamber is evacuated of air to permit effective distribution of steam. Subsequent to sterilization, the chamber is again evacuated in order to evaporate condensed steam that covers the micro-isolator and its contents. During each of these evacuations, the microprocessor control regulates the rate of vacuum draw down so that the boiling point of water in the sipper bottle is again not exceeded. This method permits micro-isolators to be sterilized with sipper bottles full of water, without losing a significant volume of water. The method of the present invention thus provides micro-isolators that are ready to use, including the drying of the micro-isolator, complete with bedding and food.

18 Claims, 4 Drawing Sheets

EXHAUST
CHAMBER STEAM
CHAMBER STEAM CONTROL
CHAMBER AIR
FILTERED AIR
VAC PUMP
JACKET STEAM
JACKET WATER
JACKET DRAIN

MICRO-ISOLATOR STEAM STERILIZATION CYCLE AND APPARATUS

BACKGROUND OF THE INVENTION

The present invention relates generally to a method of sterilization for micro-isolators, a device used to house laboratory animals, especially rodents. The invention further relates to the apparatus used in performing this sterilization cycle.

In the medical industry rodents, especially mice, are used in studies of drugs and toxicology, in which harmful side effects are observed before exposing such drugs to humans. In order to insure accurate data collection in such studies, laboratory animals must be free of contamination, and must not be exposed to any foreign bacteria or viruses. These precautions are necessary to keep the number of variables at a minimum.

In order to ensure that lab mice are free of contamination, they must live their entire lives in an environment isolated from foreign microorganisms. Lab mice are born under aseptic conditions, and they must be housed in such a sterile environment from birth until death.

As can be seen in FIG. 1, lab mice 13 are housed in a micro-isolator 10 a clear plastic cage which includes a housing 11 and a lid 12 formed with a ventilation grid, formed of a plastic mesh which includes spun-bonded polyester fabric filter paper. This filter paper permits air and humidity to freely pass between the mice and the outside environment. However, the filter paper has a mesh that filters the air down to 0.2 microns, thus preventing the admission of microorganisms, which are much larger. The micro-isolator receives and retains the essential necessities needed to maintain the mice 13, including bedding 14, and a rack 15, which supports and retains food 16 and a sipper bottle 17, which is filled with a predetermined volume of water.

Mice, contained in the micro-isolators, are maintained in a sterile environment at all times to insure isolation against outside contaminants. Nevertheless, the micro-isolator must be cleaned once or twice a week in order to provide a clean living environment for the mice. Accordingly, the mice must be transferred from the dirty micro-isolator to a fresh sterile micro-isolator, in which freshly sterilized bedding, food and sipper bottle with water have been provided.

In the prior art, the assembly of a fresh micro-isolator was a time-consuming and labor-intensive process. The micro-isolator unit itself, along with the bedding, food and sipper bottle, each had to be individually sterilized. In preparation for the lab mice, the micro-isolator and its sterilized components had to be manually assembled in a clean room environment, in a chamber with laminar air flow, in order to insure that the sterilized components were not recontaminated prior to use.

The preparation of micro-isolators must be done on-site. The maintenance of a clean room and the human resources required for this purpose adds considerable expense to the preparation of sterile microisolators. Considering that some institutions process as many as 7000 micro-isolators a week, the expense of such microisolators can add up quickly. Consequently, an apparatus and method which would permit faster preparation of sterilized micro-isolators, using less manpower, would be a very desirable advance in the art.

Some prior art practitioners have contemplated sterilizing an assembled micro-isolator, with bedding, food and sipper bottle deposited therein, prior to sterilization. However, such a procedure has presented several problems. In order to achieve efficacious sterilization, steam must be injected at temperatures of between 118°–130° C. These are temperatures of moist heat which are sufficient to destroy foreign micro organisms. At such temperatures, the water in the sipper bottle will boil at atmospheric pressure. Should the sipper bottle be permitted to boil over, the micro-isolator and its contents will be wetted, and the sipper bottle will end up nearly dry. Such conditions do not provide an acceptable environment for laboratory mice. Thus, sipper bottles have needed to be sterilized separately from the rest of the micro-isolator, in order to guard against boil over and the resulting saturation of the bedding.

Sterilization temperatures are typically achieved using a steam charge which leaves residual condensed moisture on the micro-isolator and its contents. The unit may be dried by reducing the chamber pressure to a subatmospheric level, which permits the rapid evaporation of any condensed moisture. However, such a reduction in pressure also causes the water in the sipper bottle to boil. As a result, the sipper bottles would boil over and saturate the bedding at this stage as well. This and other difficulties encountered in the prior art are overcome by the present invention.

BRIEF SUMMARY OF THE INVENTION

The apparatus of the invention comprises a sterilizer including a sterilization chamber for receiving the articles to be sterilized. The sterilization chamber is surrounded by a vessel jacket. The sterilizer includes a plurality of fluid conduits for introducing a plurality of respective fluids into the sterilizer.

The sterilization chamber includes fluid inlets, connected to the fluid conduits, for admitting vacuum, steam and compressed air, in order to effect a predetermined sterilization cycle. The vessel jacket includes inlets for admitting steam and cold water, which assist in the raising and lowering of chamber temperature during respective stages of the predetermined sterilization cycle. Each of these fluids and the vacuum are supplied by respective sources, each of which can include a pump to drive the fluid to the chamber. Each pump may operate in conjunction with a valve, which further regulates the flow of fluid or vacuum. In the present invention, the rate of fluid supply is carefully controlled by using a microprocessor unit which controls the operation of the various pumps and valves which supply fluid and vacuum to the chamber.

One or more temperature probes, in communication with the microprocessor control unit, are placed inside the chamber to monitor the load temperature. These temperature probes provide data to the microprocessor, which in turn controls the activation of the respective various fluid pumps and valves. These pumps and valves are actuated to maintain chamber pressure and temperature at a sufficient level in order to prevent the water in the sipper bottle from boiling during the course of the sterilization cycle of the present invention.

The sterilization cycle of the present invention includes an operation of the sterilizer in a manner which enables assembled micro-isolators to be sterilized and presented ready for use, including a filled sipper bottle which is sterilized along with the food and bedding. The steps of this method include a preliminary evacuation of the sterilization chamber at a controlled rate and pressure level so that the water in the sipper bottle is maintained at a reduced pressure sufficient so that the water does not boil.

After the preliminary evacuation, a steam charge is introduced at an elevated pressure so that, as temperature reaches an effective sterilization temperature, the water in the sipper bottle does not exceed the boiling point, the steam charge is maintained at the elevated temperature and pressure for a predetermined hold period so as to provide efficacious sterilization. After the hold period, the sterilization chamber is pressurized using compressed air which maintains the chamber pressure at a constant level. At this time, the vessel jacket is filled with cold water in order to effect rapid cooling of the chamber walls. The compressed air is flowed through the chamber so as to carry away heat, thus cooling the chamber and lowering the temperature of the articles contained therein, while maintaining a constant chamber pressure. At the end of this cooling stage, the temperature is lowered sufficiently so that the pressure can be reduced to the atmospheric level. At this time, the water in the vessel jacket is replaced with steam, and a post-sterilization vacuum is applied to the chamber, in order to accelerate the evaporation of any water that may have condensed inside the chamber, along with the surface of the articles contained therein. The vacuum is held at a subatmospheric level sufficient so as to not permit the water in the sipper bottle to boil. After a vacuum hold interval sufficient to effect the drying of the chamber and articles, the chamber is again restored to atmospheric pressure.

OBJECTS OF THE INVENTION

Therefore, it is an object of the present invention to provide a method and apparatus that permits the sterilization of assembled micro-isolators. Another object of the invention is to monitor and control the conditions of temperature and pressure within the apparatus so as not to allow the sipper bottle water to boil while allowing the drying of the cage, food and bedding. It is a further object of the invention to enable the sterilization of micro-isolators using fewer steps, thus reducing the time and resources required for sterilization.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims. Still other objects and advantages of the present invention will become readily apparent to those skilled in the art from the following detailed description, wherein is shown and described only a preferred embodiment of the invention, simply by way of illustration of the best mode contemplated for carrying out the invention.

DETAILED DESCRIPTION OF THE PREFERRED EMBODIMENTS

Figure 1:
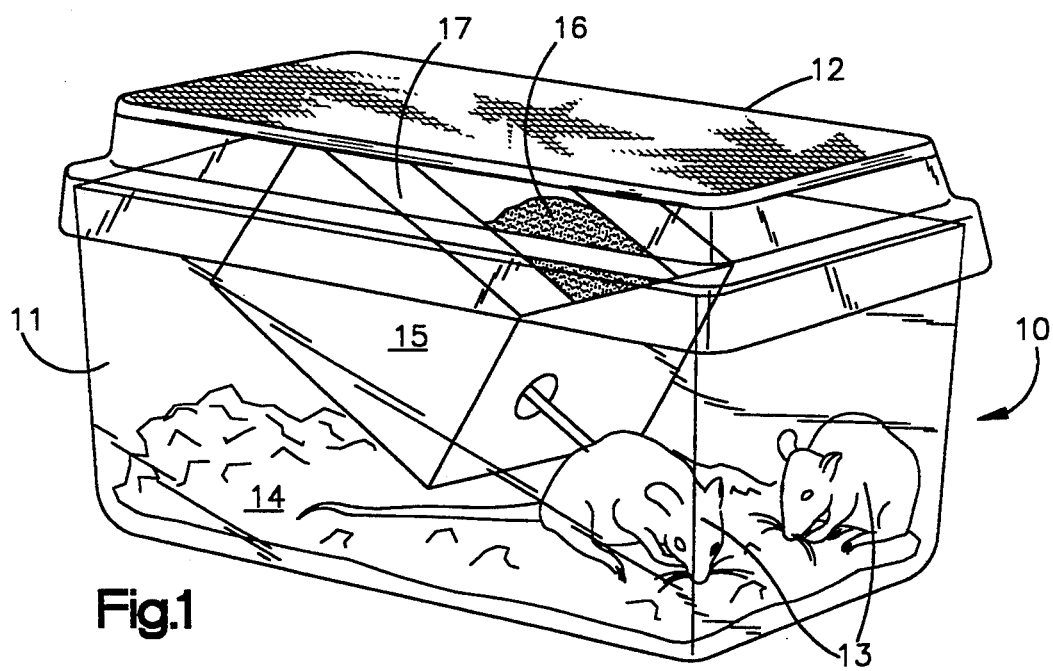
FIG. 1 is an oblique view illustrating the design and components of a micro-isolator, as are known in the art.

Now, with more particular reference to the drawings, FIG. 1 shows the micro-isolator 10 of the type which is sterilized by the present invention. The micro-isolator 10 is assembled with bedding 14, and a rack 15 which supports and retains food 16 and a sipper bottle 17, which is turned in a position which is inverted from the operational position. The sipper bottle 17 is retained in an inverted position for the entire sterilization cycle. In order to effect sterilization, one or more assembled micro-isolators 10 are inserted into the sterilizer 100, shown generally in FIG. 2a and 2b.

Figure 2A:
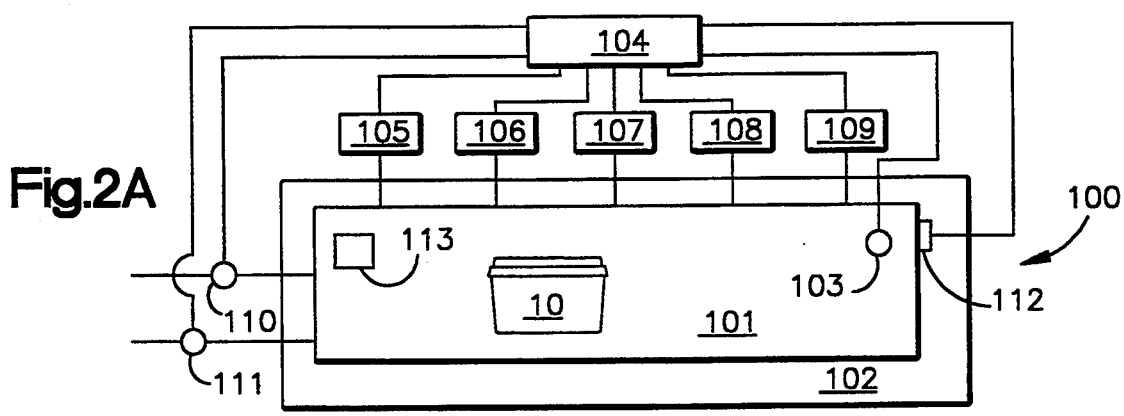
FIGS. 2a and 2b are schematic views illustrating the sterilizer of the present invention, showing the components and their arrangement.
Figure 2B:
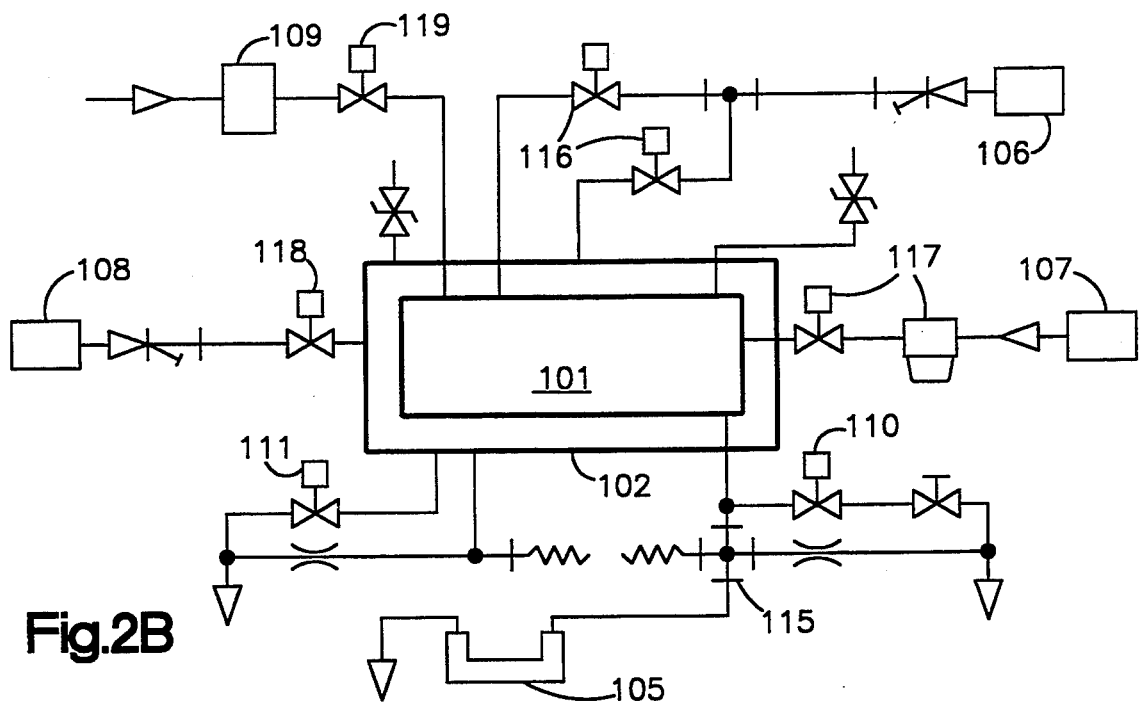

As seen from FIGS. 2a and 2b, the sterilizer 100 includes a sterilization chamber 101 into which are inserted the one or more micro-isolator units to be sterilized. The sterilization chamber 101 is fluidly connected to a plurality of fluid sources 105, 106, 107, 108, 109, which provide fluids of various temperatures and pressures so as to effect the sterilization of the micro-isolators 10 contained therein.

The sterilization chamber 101 is substantially surrounded by a vessel jacket 102 into which is injected fluids of varying temperatures, in order assist in the raising and lowering of temperatures within the sterilization chamber 101. The vessel jacket 102 helps maintain the temperature in the sterilization chamber 101 since it provides thermally controlled exterior layer to the chamber.

Connected respectively to the sterilization chamber 101 and vessel jacket 102 are a plurality of fluid sources. Vacuum source 105 is used to evacuate the sterilization chamber 101 to a predetermined subatmospheric level as is necessary during the sterilization cycle. Steam source 106 provides saturated steam to both the sterilization chamber 101 and the vessel jacket 102. The saturated steam provided by the steam source 106 is used to provide "moist heat," in the chamber 101 at a temperature level sufficient to kill microorganisms.

Compressed air source 107 supplies cooler compressed air which has been filtered and sterilized to the sterilization chamber 101. The compressed air carries away a portion of the heat from the chamber 101 and its contents, thus cooling it down after the application of steam. The compressed air also maintains the chamber pressure at its elevated level so as to prevent the water in the sipper bottles 17 from boiling. In order to hasten the cooling process, steam is removed from the vessel jacket, and cold water from the cold water source 108 is supplied to the vessel jacket 102, which reduces the temperature of the walls of the sterilizer. Finally, the sterilization chamber 101 is connected to a filtered air supply 109 which supplies sterile air and restores pressure within the chamber 101 to ambient atmospheric pressure, 14.7 psia.

The respective sources 105, 106, 107, 108 and 109 can be, in the preferred embodiment, conventional pumps of the type commonly known in the art for supplying air, liquid and vacuum. Access to the sterilization chamber 101 and vessel jacket 102 can be controlled by activation of such pumps alone, or in combination with respective valves 115, 116, 117, 118 and 119 which can regulate access of these fluids, as are also known in the art. Filtered air supply 109 may simply be a filter, vented to atmosphere, which removes microorganisms and is regulated by a valve 119. In order to effect uniform heating and cooling throughout the sterilization cycle, an internal fan 113 may be inserted in the chamber 101 in order to circulate the air, maintaining uniform temperature at all times within the chamber 101.

In order to provide a sterilization cycle in accordance with the objects of the invention, the activation of the sources (with their respective pumps and valves) is coordinated with a microprocessor control 104 which activates and deactivates the sources in order to execute the sterilization steps. The microprocessor control 104 is of the type commonly known to those in the art, and is programmed to control the operation of the system using conventional programming techniques. The microprocessor control 104 receives data from a temperature probe 103 inserted in a representative sample region of the sterilization chamber 101, e.g. a sipper bottle 17 in a "cold spot" of the chamber. The temperature probe 103 can be either a thermocouple or a Resistance Temperature Detector (RTD).

The temperature probe 103 transmits temperature data to the microprocessor control 104, which then uses that data to selectively control the activation of the steam source 106, in order to regulate chamber temperature so that the boiling point of water is not exceeded as chamber temperature is varied. The microprocessor control 104 is also used to open drain vents 110, 111 which are used to drain and vent to the atmosphere respectively the sterilization chamber 101 and the vessel jacket 102. Pressure within the chamber 101 is monitored by a pressure transducer 112 which is mounted to the side wall of the chamber 101. Like the temperature probe 103, the pressure transducer 112 is in communication with microprocessor control 104 and supplies data regarding the chamber pressure.

Figure 3:
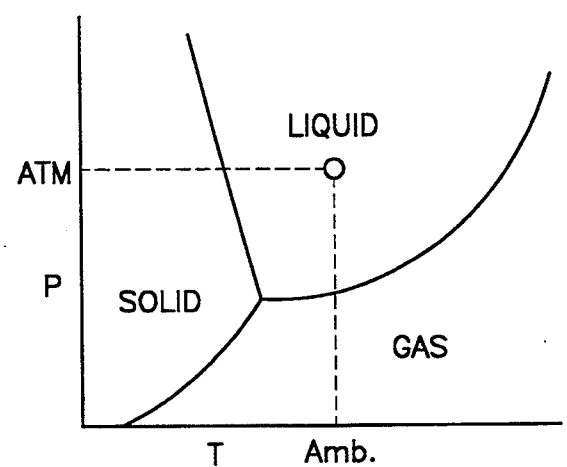
FIG. 3 is the phase diagram for water, showing how water varies between solid, liquid and gaseous phases with varying conditions of pressure and temperature.

FIG. 3 illustrates the phase diagram for water, showing how water varies between solid, liquid and gaseous phases according to varying conditions of temperature and pressure. In the method of the present invention, temperatures in the sterilization chamber 101 vary significantly, from room temperature ($\approx 20°$ C.) to a sterilization temperature effective to destroy microorganisms (between 118° and 130° C.). As temperatures vary, the present invention provides a chamber pressure greater than that needed to maintain the water in the sipper bottle 17 in a liquid phase. Should too low a pressure be provided, the phase conditions in the sterilization chamber 101 will cross the boundary into the gaseous phase, and the water in the sipper bottle 17 will boil over, saturating the micro-isolator and its contents, compromising the living quarters and food and leaving the sipper bottle 17 with an insufficient volume of water to sustain a lab animal.

In quantified measurements of sterilization, heat sterilization of microorganisms is a function of the heat of microorganism exposure, the number of microorganisms and the heat resistance of the microorganisms. These quantification techniques are outlined in *PDA Technical Monograph No.* 1, "Validation of Steam Sterilization Systems", pp. 23–36, published by the Parenteral Drug Association Research Committee and Task Groups, the disclosure of which is hereby incorporated by reference.

As is clear from *PDA Technical Monograph No.* 1, sterilization is quantified by measuring "lethality" of microorganisms on objects to be sterilized. "Lethality" is given as values of "$F_o$", a function which correlates sterilization temperatures and time spent at sterilization temperature with a reduction in microorganism populations. Lethality is measured by the function:

$$F_o = D \,(\log_{10} A - \log_{10} B)$$

where
  $D$ = the time at a given temperature required to reduce the microorganisms to 1/10 their initial levels;
  $F_o$ = the equivalent time at a standard temperature of 121° C. delivered to an article for the purpose of sterilization;
  $(\log_{10} A - \log_{10} B)$ = The spore log reduction
where:
  $A$ = The initial number of microorganisms
  $B$ = The number of spores surviving the heat treatment The $F_o$ values provide a convenient standard for measuring the efficacy of sterilization, since lower temperatures can receive longer sterilization times and higher temperatures can receive shorter sterilization times. The $F_o$ values give a standard quantity of microorganism kill, given a variance of temperature and sterilization cycle time.

Figure 4A:
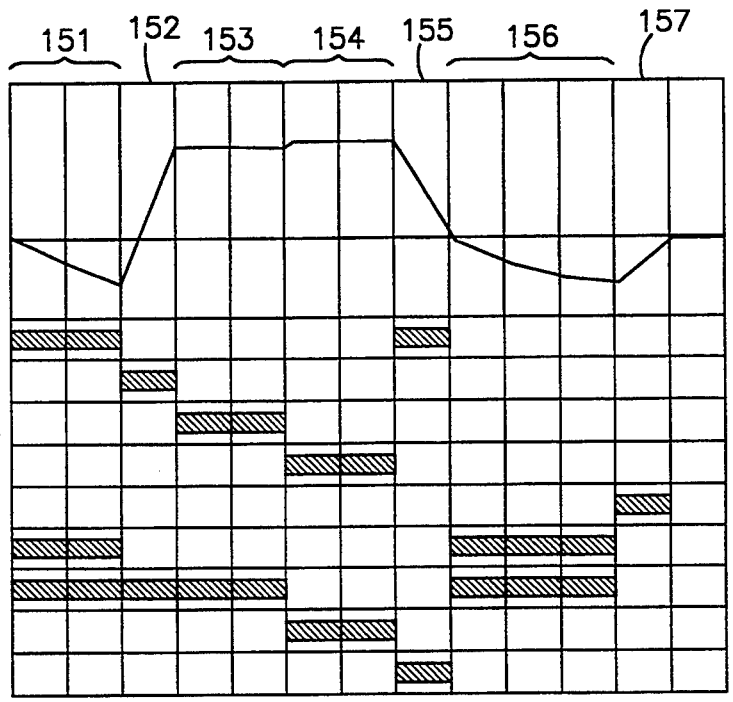
FIGS. 4a and 4b illustrate the pressure variation over time in a preferred embodiment of the sterilization cycle according to the present invention.
Figure 4B:
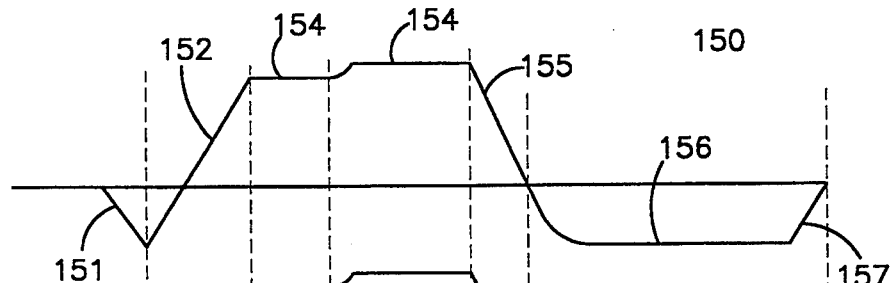

FIGS. 4a and 4b illustrate a first preferred embodiment of the sterilization cycle 150 of the present invention, illustrating the variations in chamber pressure over time. This cycle includes several stages which permit assembled micro-isolators to be sterilized and presented ready for use, including a filled sipper bottle 17 which is sterilized with the rest of the unit. FIG. 4a includes a cycle graph in which the solid line indicates which fluid source or component is activated.

At the start of the present sterilization cycle, the chamber 101 is pre-heated by admitting steam into the vessel jacket 102. The temperature of the jacket 102 is controlled between 110°–121° C. using a jacket temperature probe (not shown) which is also in communication with the microprocessor control 104. The microprocessor control 104 selectively varies the activation of the steam source 106 to control jacket temperature in response to data from the jacket probe.

Prior to admitting steam sterilant into the sterilization chamber, most of the air in the chamber 101 must be evacuated. Ordinary air is an excellent thermal insulator. As steam sterilant is introduced into the sterilization chamber, any air present in the chamber can insulate the objects or areas to be sterilized from direct contact with the saturated steam. Further, the air mixes with the steam, lowering its temperature below the desired level for sterilization. Also, pockets of air which become heated to the temperatures of saturated steam are not as effective at transferring heat from steam. In "hot air" sterilizers, higher temperatures and longer sterilization times are required. Therefore, it is necessary to remove as much air as possible prior to the injection of saturated steam sterilant.

In order to remove the air from the chamber 101 prior to sterilization, the present invention includes a preliminary vacuum (pre-vac) state 151. The microprocessor control 104 is used to activate the vacuum source 105, which removes air, lowering the pressure to a desired subatmospheric level by exhausting the air from the chamber. The vacuum source 105, may be, for example, a vacuum pump, as are known in the art. By monitoring both the temperature indicated by the probe 103, and pressure indicated by the pressure transducer 112, the microprocessor 104 varies the duty cycle of the vacuum pump, selectively activating and deactivating the vacuum pump to maintain chamber pressure at a subatmospheric level which maintains the sipper bottle water in liquid phase. Such precise micro-processor control of the duty cycle of the vacuum pump insures that too deep a vacuum is not drawn down so that chamber pressure never crosses the phase boundary for a given temperature. Exemplary preferred subatmospheric levels 151 for particular temperatures are as follows:

| Temperature | Pressure |
|---|---|
| 40° C. | 1.1 psia |
| 60° C. | 2.9 psia |
| 70° C. | 4.5 psia |
| 80° C. | 6.9 psia |

Microprocessor control of the preliminary vacuum stage 151 enables the present invention to maintain a fine degree of control over the vacuum pump. Thus, the present invention enables the air to be quickly removed, which shortens cycle time while not affecting the water in the sipper bottle 17.

After the pre-vac stage 151, the microprocessor 104 initiates the steam charge stage 152. Steam from the steam source 106 is admitted into the chamber 101 to accelerate the warming process. The steam raises the temperature to a sterilization temperature between 118°-130° C., in the preferred embodiment, about 121° C. Since 100° C. is the boiling point of water at atmospheric pressure, the steam is introduced so as to raise the pressure level above atmospheric, to a level which is sufficient to maintain water in liquid phase at 121°, for example, about 28-33 psia, so as to prevent the water in the sipper bottle 17 from boiling. The pressure transducer 112 supplies the pressure data so that the microprocessor control 104 can maintain the steam charge at optimum pressure.

The steam charge is maintained within the sterilization chamber 101 for a predetermined sterilant hold period of about 1-20 minutes, or about 8-25 $F_o$ values. In the preferred embodiment, the period is about 5 minutes or 15 $F_o$ values. This period, the exposure stage 153, is necessary to insure an efficacious sterilization of all foreign microorganisms using moist heat with a Sterility Assurance Level (S.A.L.) of $10^{-6}$ (as is practiced by those of ordinary skill in the art.). During the exposure stage 153, temperature and steam pressure are maintained at approximately 121° and 28-33 psia respectively, in order to maintain the sipper bottle water in its liquid phase. This may be accomplished by controlling the steam, such that additional steam is injected at periodic intervals in order to maintain the elevated conditions of temperature and pressure in response to signals from the probe 103 and the transducer 112.

At the end of the exposure stage 153, the contents of the sterilization chamber 101 are sterile. The exposure stage 153 is followed by the cooling stage 154, where the pressure is raised to 34-38 psia using a flow of compressed air or any other suitable gaseous fluid. The micro-isolators 10 and all their contents are at an elevated temperature following sterilization. Therefore, according to the present invention, the pressure 154 is not lowered to atmospheric pressure until the chamber temperature is first lowered. Compressed air is flowed through the chamber 101 in order to remove the steam as the vessel jacket 102 is emptied of steam and filled with cold water. Consequently, much of the chamber heat is carried away by these cooling steps. In the preferred embodiment, the flow of compressed air is maintained at 34-38 psia so that chamber pressure is not lowered during the exhaustion of the steam. The temperature of the compressed air, in the preferred embodiment, is room temperature, 20° C. At the end of the cooling stage 154, temperature of the micro-isolator and water sipper bottle 17 can be at a desired temperature of 60°-80°, which is below the boiling point of water at most common temperatures. At this point, the temperature probe 103 indicates the desired temperature, signalling the next stage.

In an alternative embodiment, the air pressure is lowered as the chamber temperature comes down. Any combinations of temperature and pressure may be contemplated as long as the chamber pressure is not lowered so quickly as to the cross the phase boundary into the gaseous state, resulting in the boiling of water.

After the cooling stage 154, there remains a considerable amount of moisture clinging to the micro-isolator 10 and its contents, especially the bedding 15 and the food 16. This moisture is the result of the steam, a portion of which condenses on all the articles in the sterilization chamber. In order to eliminate this moisture from the chamber, an exhaust and vacuum drying stage is implemented.

During the exhaust stage 155, the chamber pressure is equalized to ambient by exhausting the chamber through the vacuum source 105. When the pressure transducer 112 indicates that ambient pressure is achieved, the microprocessor control 104 commands a controlled vacuum to be again drawn down. The second application of controlled vacuum initiates the vacuum drying stage 156. The microprocessor control 104 is used to regulate the action of the vacuum source 105, so as to draw down chamber pressure without going so low as to cross the phase boundary for the temperature indicated by the temperature probe. The chamber pressure is lowered again to a subatmospheric level of between 2.0 to 7.4 psia, in the preferred embodiment, 4.5 psia for a water bottle temperature of about 70° C. This subatmospheric level is maintained for a predetermined dwell time, from about 1-90 minutes, in the preferred embodiment about 60 minutes.

During the vacuum drying stage 156, the activation of the vacuum source 105 is again controlled in response to temperature and pressure signals so that the water in the sipper bottle 17 does not boil. However, evaporation of any moisture within the chamber is enhanced by the lower subatmospheric pressure. The surfaces of the micro-isolator 10, as well as the bedding 14 and food 16 contained therein, possess quite a bit of heat, enough to supply the latent heat of vaporization to the moisture adhering to the micro-isolator 10 and its components. The subatmospheric pressure accelerates the rate of evaporation, and thus the drying of the assembled micro-isolators. In order to supply additional heat the chamber 101 and its contents, the cold water is drained and steam is again admitted to the vessel jacket 102.

After the vacuum drying stage 156, the chamber pressure is restored to atmospheric level, 14.7 psia. This part of the cycle is the air break stage 157. Filtered, sterile air is supplied to the chamber 101 through the filtered air supply 109, which restores the chamber 101 to ambient pressure. By this time, the micro-isolator 10 and its contents are sterile and dry and can be removed from the sterilization chamber. Rather than employ the complicated micro-isolator assembly steps used in the prior art, the operator simply opens the micro-isolator lid 12, inverts sipper bottle 17 into the operational position, and puts the laboratory animal 13 into the sterile micro-isolator 10. Consequently, the present invention represents a tremendous savings in human time and intervention.

In employing the microprocessor-controlled process of the present invention, no more than 5% of the water in the sipper bottle 17 is typically lost to evaporation during the variations in temperature and pressure. Studies of the food 16 have shown that its nutritional value is nearly unaffected by passing through this sterilization cycle. Further, the food is neither too wet nor too dry so as to be unpalatable to the laboratory animals 13. Also, objectionable clumping of the food 16 does not occur.

Figure 5A:
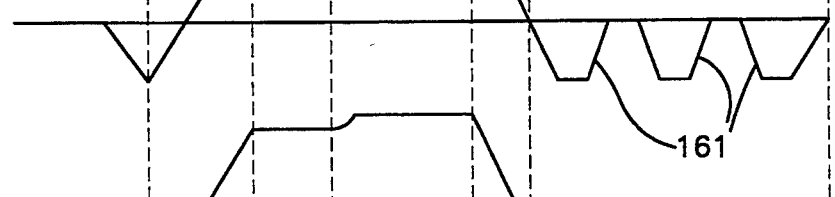
FIG. 5a, 5b and 5c, illustrate the pressure variation over time of other preferred embodiments of the sterilization cycle according to the present invention.
Figure 5B:
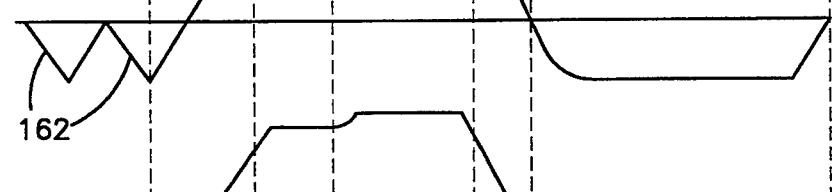
Figure 5C:
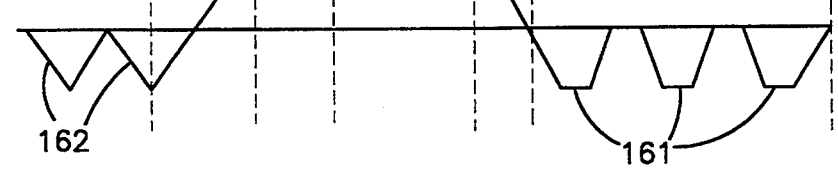

FIGS. 5a, 5b and 5c illustrate the second preferred embodiments of the present invention. The inventors have discovered that the pre-vac 151 and vacuum dry 30 stages of the sterilization cycle can be accelerated by the application of vacuum pulses. During each pulse, the chamber is evacuated and restored to atmospheric pressure, 14.7 psia.

For pulses during the pre-vac stage, chamber pressure is lowered to 2.5 psia. Steam is admitted to restore atmospheric pressure, and a second vacuum pulse is applied. By applying a number of these pulses, air may be evacuated more quickly from the chamber 101. During each pulse, the steam is mixed with the air that remains in the chamber. After each pulse, the air is diluted with saturated steam. In this manner, air is quickly removed from the chamber 101.

During the vacuum drying stage, the chamber pressure is reduced to 4.4 psia, and after a dwell time of 1–10 minutes, preferably about 5 minutes, chamber pressure is restored to atmospheric pressure with filtered air from the air source 109. Each pulse is applied so as to insure that the partial pressure of water vapor in the chamber is continually kept at a minimum, as water evaporates from the micro-isolator 10 and articles. By applying several vacuum pulses, the physical removal of evaporated moisture from the micro-isolators 10 is greatly accelerated, reducing the vacuum drying stage from a preferred 60 minutes to a preferred 30–45 minutes.

A number of sterilization cycles are contemplated which can combine the vacuum pulse step with non-pulse evacuations. FIG. 5a illustrates applying vacuum pulses 161 to the vacuum dry stage, while FIG. 5b shows vacuum pulses 162 only during the pre-vac stage. FIG. 5c shows vacuum pulses during both stages. It has been discovered that a variable number of pulses may be chosen, varying according to the number of micro-isolators sterilized in each load. Up to 99 pulses may be applied per load.

The time spent at each stage of the sterilization cycle varies in accordance with the size of the sterilization chamber 101 and the number of micro-isolators within the chamber. The microprocessor control 104 contains a "cycle skeleton" including the stages of the cycle and basic parameters for operation. It is incumbent upon the operator to perform a validation procedure to determine the specific parameters of temperature, pressure and time for a variety of different cycles, which each may vary according to the number of micro-isolators sterilized by a given cycle.

The validation procedure is a data collection procedure wherein several cycles are run for a number of specific sample loads, each including a given number of micro-isolators. In the validation procedure, temperatures are measured in all parts of the sterilization chamber in order to prepare a "map" showing the thermal distribution for each sample load. The parameters determined by this validation procedure are stored in the memory of the microprocessor control 104, and may be recalled to perform specific predetermined sterilization cycles, each tailored to the operators specific needs. This permits a highly efficient, reproducible result for each sterilization load.

To assist in the validation procedure, the probe 103 is inserted into one of several sipper bottles 17. The sipper bottle 17 (which is the hardest to heat item) is located in the "cold spot" of the sterilization chamber 101, that is, the location which is determined to have the lowest heat as measured in $F_o$ values. At the end of the sterilization cycle, the probe is disconnected from the sipper bottle 17. However, in order to insure that sterilization is not compromised upon disconnection, the probe may alternatively be inserted into a "dummy" sipper bottle, which is then suspended at the "cold spot". By performing the validation procedure, the sterilization cycle can be performed more efficiently for a number of specific loads.

Figure 6:
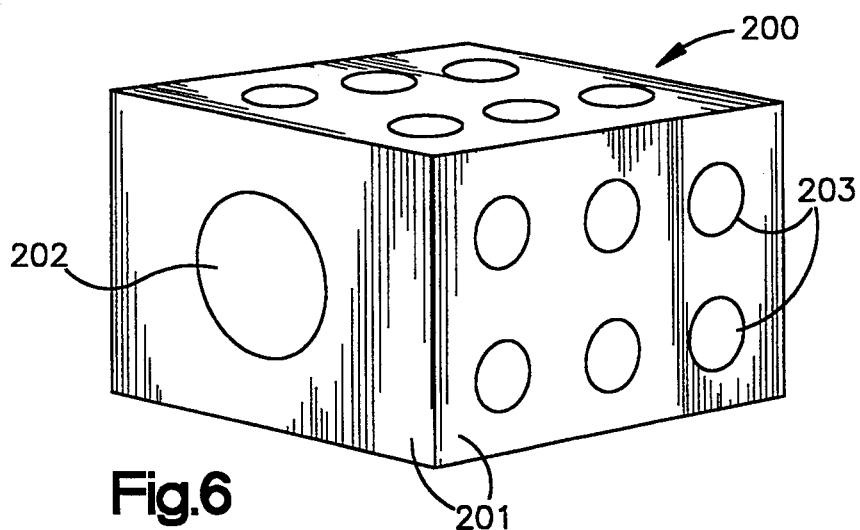
FIG. 6 is an oblique view illustrating the general form of the transfer box which is used with the present invention.

The present invention also permits the use of a transfer box in which several micro-isolators can be inserted and sterilized at once. Such a transfer box 200 is shown in FIG. 6. This transfer box 200 includes walls 201 and a door 202 through which micro-isolators can be transferred. The transfer box 200 also includes apertures 203, covered with filter paper, which like the micro-isolators, permit the passage of air and steam sterilant, but which have a porosity too small to admit microorganisms.

Several micro-isolators can be inserted into this transfer box 200, which is then inserted into the sterilizer 100. Upon sterilization, the entire contents of the transfer box 200 will be sterilized and it can then be removed and transported. Since the filter paper holes 203 prevent the passage of microorganisms, the transfer box 200 can be removed to a non-sterile environment, while still maintaining the integrity of the sterile volume within the box.

Figure 7:
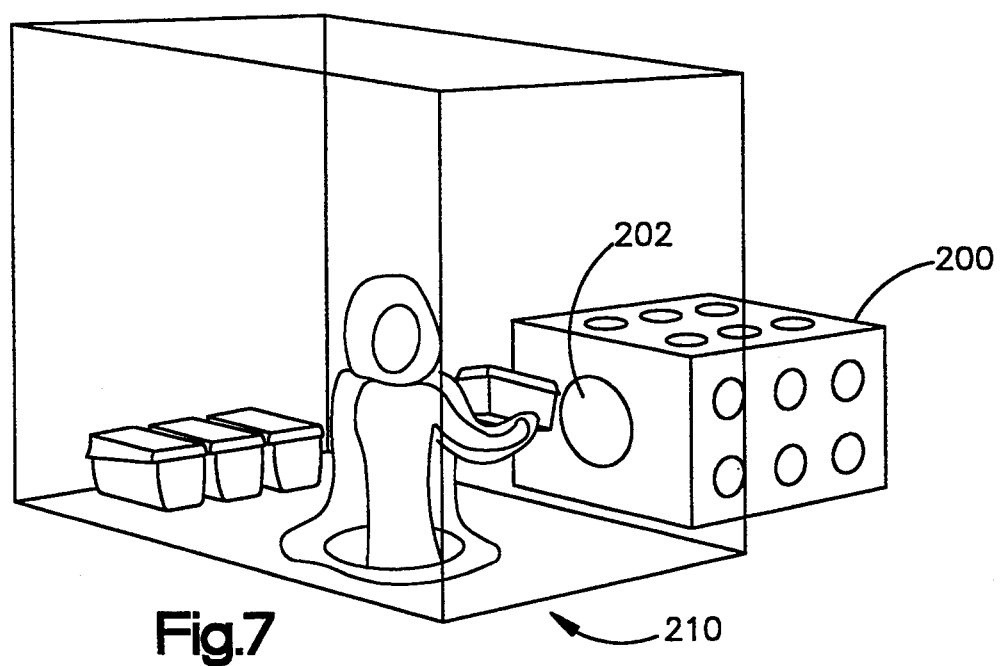
FIG. 7 depicts the operation of the transfer box in transporting sterile micro-isolators to a remote sterile environment.

As seen in FIG. 7, the door 202 of the transfer box may be fitted with a pass-through door of the type commonly found in the art for maintaining a removable sterile connection between two sterile volumes, wherein at least one such volume is movable. The present method provides that micro-isolators be sterilized at a remote location, and transferred through non-sterile areas where it can be connected to another sterile volume 210 where the micro-isolators can be removed. With the present method, this entire procedure can be effected with no human intervention prior to the insertion of the laboratory animals 13 into their fresh microisolators. Such mobility has not been available until the development of the present invention.

As will be realized, the invention is capable of other and different embodiments, and its several details are capable of other and different embodiments, and its several details are capable of modifications in various obvious respects, all without departing from the invention. Accordingly, the drawings and description are to be regarded as illustrative in nature, not as restrictive. The embodiments of the invention in which an exclusive property of privilege is claimed are defined as follows.

What is claimed is:

1. A method of sterilizing a container including an article containing water comprising the steps of:
    providing a sterilization chamber for receiving a container including an article containing water to be sterilized;
    introducing steam into said chamber for raising chamber temperature to a predetermined sterilization temperature wherein the steam is introduced at a predetermined pressure sufficient to avoid boiling the water in the article;
    maintaining the temperature and pressure levels for a sufficient interval so that sterilization of said container and article containing water is effected;
    exhausting the sterilization chamber of steam while maintaining that temperature and pressure levels within the chamber below the boiling point of water by introducing compressed gas into the chamber in order to exhaust the steam and lower the temperature so as to cool the container and article, said compressed air is introduced at a predetermined pressure sufficient to avoid substantially boiling the water at the maintained temperature;
    evacuating said chamber to a subatmospheric pressure, said subatmospheric pressure being controlled sufficiently to evaporate steam condensate that adheres to said chamber and articles, but sufficient to avoid boiling the water in the article; and
    restoring chamber pressure to atmospheric level.

2. The method of claim 1 further comprising the step of:
    prior to said steam introducing step, providing a preliminary evacuation of said chamber to lower chamber pressure to an initial subatmospheric level at such a rate that the boiling point of water is not exceeded for the temperature of the chamber.

3. The method according to claim 2 wherein the initial subatmospheric level is 1.0–7.4 psia.

4. The method according to claim 2 wherein said preliminary evacuations are followed by a predetermined number of vacuum pulses, wherein for each pulse, the chamber pressure is lowered to the initial subatmospheric level and then raised again to atmospheric level.

5. The method according to claim 1 wherein said container is a micro-isolator including accommodations for laboratory animals.

6. The method according to claim 5 wherein the accommodations include a sipper bottle which contains water and is exposed to the pressure of the chamber for the entire sterilization cycle.

7. The method according to claim 1 wherein the subatmospheric level is 2.0–7.4 psia.

8. The method according to claim 1 wherein said steam introducing step raises chamber temperature to at least 118° C. and chamber pressure to at least 28 psia.

9. The method according to claim 8 wherein the predetermined sterilization interval is about 5 minutes or 15 $F_o$ values.

10. The method according to claim 8 wherein the compressed air during the exhausting of the sterilization chamber is at a level sufficient to raise and maintain chamber pressure to at least 34 psia.

11. The method according to claim 1 wherein the chamber pressure is maintained at the subatmospheric level for a predetermined dwell time, sufficient to effect the evaporation of steam condensate.

12. The method according to claim 11 wherein the dwell time is 1–90 minutes.

13. The method according to claim 1 wherein said evacuation further comprises the application of a predetermined number of vacuum pulses, wherein for each pulse, the chamber pressure is lowered to the subatmospheric level and then raised again to atmospheric level.

14. A method of providing a sterilization cycle for a plurality of articles, comprising the steps of:
    providing a transfer box into which are inserted a plurality of articles;
    providing a sterilization chamber for receiving the transfer box including said plurality of articles to be sterilized;
    introducing a steam charge into said chamber for raising chamber pressure and chamber temperature to predetermined levels wherein temperature and pressure are maintained for a sufficient interval so that sterilization of the transfer box including said plurality of articles is effected;
    exhausting the sterilization chamber of steam while introducing a flow of compressed air such that temperature and pressure levels within the chamber do not exceed the boiling point of water;
    providing a drying evacuation of said chamber in order to lower chamber pressure to a subsequent subatmospheric level, while controlling temperature so that the boiling point of water is not exceeded, said subsequent subatmospheric level being sufficient to evaporate steam condensate that adheres to said chamber and articles; and
    providing an air break to restore chamber pressure to atmospheric level;
    removing said transfer box from the sterilizer into a non-sterile environment, whereby said plurality of articles remain sterile while inside the unopened transfer box.

15. The method of claim 14 comprising the step of:
    prior to the introduction of the steam charge, providing a preliminary evacuation of said chamber to lower chamber pressure to a initial subatmospheric level at such a rate that the boiling point of water is not exceeded for the temperature of the chamber.

16. The method according to claim 14 wherein said container is a micro-isolator and said plurality articles includes accommodations for laboratory animals, further including food, bedding and a sipper bottle, wherein the sipper bottle includes water which is exposed to the pressure of the chamber for the entire sterilization cycle.

17. A method of sterilizing a container including an article containing water, comprising the steps of:

providing a sterilization chamber for receiving a container including an article containing water to be sterilized;

monitoring a temperature of the article containing water so as to produce a monitored temperature;

introducing steam into said chamber for raising chamber temperature to a predetermined temperature sufficient to insure sterilization of the container and articles wherein the steam is introduced into said chamber at a predetermined pressure sufficient to avoid boiling the water in the article in response to the monitored temperature;

maintaining the temperature and pressure levels for a sufficient interval so that sterilization of the container and article containing water is effected;

exhausting the sterilization chamber of steam and cooling the chamber while maintaining the pressure within the chamber at a sufficient level to avoid boiling the water in response to the monitored temperature;

evacuating said chamber to a subatmospheric pressure in response to the monitored temperature, said subatmospheric pressure is controlled sufficiently to evaporate steam condensate that adheres to said chamber and articles but sufficient to avoid boiling the water in the article; and restoring chamber pressure to atmospheric level.

18. A method of sterilizing a container including an article containing water comprising the steps of:

providing a sterilization chamber for receiving a container including an article containing water to be sterilized;

evacuating said chamber to an initial subatmospheric pressure sufficient to avoid boiling the water in the article;

introducing steam into said chamber for raising chamber temperature to a predetermined sterilization temperature wherein the steam is introduced at a predetermined pressure sufficient to avoid boiling the water;

maintaining the temperature and pressure levels for a sufficient interval so that sterilization of said container and article containing water is effected;

exhausting the sterilization chamber of steam by introducing compressed air into the chamber in order to lower the temperature so as to cool the container and articles, said compressed air is introduced at a predetermined pressure sufficient to avoid boiling the water;

evacuating said chamber to a subatmospheric pressure, said subatmospheric pressure is controlled sufficiently to evaporate steam condensate that adheres to said chamber and article but sufficient to avoid boiling the water in the article; and restoring chamber pressure to atmospheric level.

* * * * *